US008158339B2

(12) United States Patent
Ilyin et al.

(10) Patent No.: US 8,158,339 B2
(45) Date of Patent: Apr. 17, 2012

(54) METHOD OF PRESERVING A PLATELET CONCENTRATE UNDER ELEVATED XENON CONCENTRATION AND PRESSURE WITH REFRIGERATION

(75) Inventors: Ilya Y. Ilyin, Wayland, MA (US); Maria G. Tkachman, St. Petersburg (RU); Maria E. Urusova, Gatchina (RU); James S. Jones, St. Simons Land, GA (US); William E. Grieshober, East Amherst, NY (US); Semyon Kogan, Newton, MA (US); Pavel Butylin, St. Petersburg (RU); Rostislav Khorenyan, St. Petersburg (RU)

(73) Assignee: Rich Products Corporation, Buffalo, NY (US)

( * ) Notice: Subject to any disclaimer, the term of this patent is extended or adjusted under 35 U.S.C. 154(b) by 454 days.

(21) Appl. No.: 12/498,857

(22) Filed: Jul. 7, 2009

(65) Prior Publication Data

US 2010/0009334 A1   Jan. 14, 2010

Related U.S. Application Data

(60) Provisional application No. 61/078,585, filed on Jul. 7, 2008, provisional application No. 61/160,945, filed on Mar. 17, 2009.

(51) Int. Cl.
*A01N 1/02* (2006.01)
*A01N 63/00* (2006.01)
(52) U.S. Cl. .................................. 435/2; 424/93.72
(58) Field of Classification Search .......................... None
See application file for complete search history.

(56) References Cited

U.S. PATENT DOCUMENTS

| 3,228,838 | A | 1/1966 | Rinfret |
|---|---|---|---|
| 3,344,617 | A | 10/1967 | Rinfret |
| 4,473,552 | A | 9/1984 | Jost |
| 4,946,326 | A | 8/1990 | Schvester |
| 5,108,656 | A | 4/1992 | Schvester |
| 5,237,959 | A | 8/1993 | Bergeron |
| 5,309,868 | A | 5/1994 | Tomiyama |
| 5,555,845 | A | 9/1996 | Flynn |
| 5,597,599 | A | 1/1997 | Smith |
| 5,622,867 | A | 4/1997 | Livesey |
| 6,238,716 | B1 | 5/2001 | Prins |
| 6,342,261 | B1 | 1/2002 | Spencer |
| 2003/0158507 | A1 | 8/2003 | Serebrennikov |
| 2005/0002873 | A1 | 1/2005 | Harmon |
| 2005/0136125 | A1 | 6/2005 | Roth |
| 2005/0147692 | A1 | 7/2005 | Roth |
| 2005/0170019 | A1 | 8/2005 | Roth |
| 2007/0078113 | A1 | 4/2007 | Roth |
| 2008/0031971 | A1 | 2/2008 | Petzelt |
| 2008/0085329 | A1 | 4/2008 | Roth |
| 2008/0131514 | A1 | 6/2008 | Truong-Le |
| 2008/0171093 | A1 | 7/2008 | Roth |
| 2008/0171725 | A1 | 7/2008 | Roth |
| 2008/0171726 | A1 | 7/2008 | Roth et al. |
| 2009/0011051 | A1 | 1/2009 | Roth et al. |
| 2009/0286220 | A1 | 11/2009 | Sheleg |

FOREIGN PATENT DOCUMENTS

| EP | 0815745 | 7/1998 |
|---|---|---|
| WO | WO9319629 | 3/1993 |
| WO | WO2005039600 | 10/2004 |
| WO | WO2008018673716 | 10/2004 |
| WO | WO2005041655 A2 | 2/2005 |
| WO | WO2005039291 A2 | 5/2005 |
| WO | WO2005041656 A2 | 5/2005 |
| WO | WO2006113914 A2 | 10/2006 |
| WO | WO2008040002 A2 | 4/2008 |

OTHER PUBLICATIONS

Phlip et al., "Effects of elevated pressures of inert gases on cytosolic free Ca2+ of human platelets stimulated with ADP", Cell Calcium 14 : 525-529 (1993).*
D. Poppert, et al. The cryoprotective properties of various gases in kidney preservation, Zschr. Urol. vol. 66, 481-488 (1973) [In German].
D. Poppert, et al. The cryoprotective properties of various gases in kidney preservation, Zschr. Urol. vol. 66, 481-488 (1973) [English translation of German reference].
De Rossi et al.,. Xenon does not affect human platelet function in vitro Anesth Analg. Sep. 2001;93 (3):635-40.
Sergey Sheleg, et al. Hugh Nixon, Bruce Cohen, David Lowry and Mikhail Nedzved, Cardiac Mitochondrial Membrane Stability after Deep Hypothermia using a Xenon Clathrate Cryostasis Protocol—an Electron Microscopy Study Int J Clin Exp Pathol (2008) 1, 440-447.
Shcherbakov P.V., Telpuhov V.I. Gas Influenced Immortality. Chemistry and Life 2006;8:34-39 (in Russian; English translation obtained from www.cryostasis.com/Translate_Scherbakov_Paper.pdf).
Lozano M. (2008) Platelets come back in from the cold. Blood, vol. 111, No. 6, p. 2951.
Petzelt C, et al., Blom P, Schmehl W, Mullera J, Kox WJ (2003) Prevention of neurotoxicity in hypoxic cortical neurons by the noble gas xenon. Life Sciences, vol. 72, pp. 1909-1918.
Hans H. Wandall, et al. Galactosylation does not prevent the rapid clearance of long-term, 4° C.-stored platelets, Blood 2008 111: 3249-3256.
Emma C. Josefsson et al. Platelet Storage Temperature—How Low Can We Go? Transfu. Med. Hemother. (2007); 34:253-261.
Sanders, R. et al. Xenon: elemental anesthesia in clinical practice, British Medical Bulletin (2005) 71: 115-135.

* cited by examiner

*Primary Examiner* — Sandra Saucier
(74) *Attorney, Agent, or Firm* — Hodgson Russ LLP

(57) ABSTRACT

Provides are improved methods for storing platelets and compositions that contain stored platelets for use in transfusions. The method entails obtaining a platelet concentrate from blood obtained from an individual and holding the platelet concentrate in at refrigerated temperatures under an atmosphere having a pressure of from 3.5 to 5 bars comprising more than 65% xenon and for at least one week. Also provided is a refrigerated composition that contains a platelet concentrate, wherein the platelet concentrate contains xenon, and wherein the platelet concentrate has been isolated from an individual for at least seven days.

14 Claims, 1 Drawing Sheet

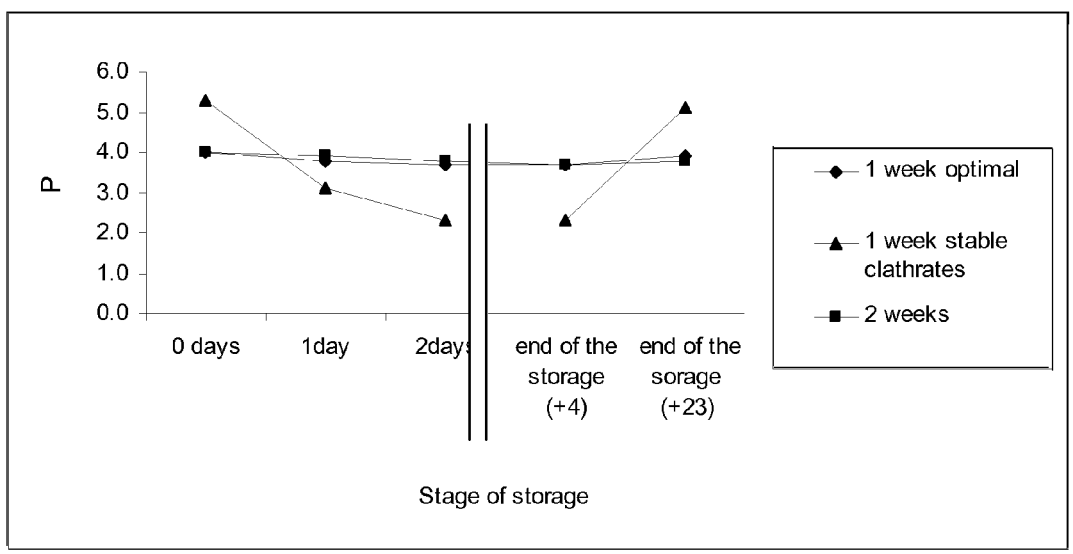

METHOD OF PRESERVING A PLATELET CONCENTRATE UNDER ELEVATED XENON CONCENTRATION AND PRESSURE WITH REFRIGERATION

This application claims priority to U.S. application No. 61/078,585, filed Jul. 7, 2008, and U.S. application No. 61/160,945, filed Mar. 17, 2009, the disclosures of each of which are hereby incorporated by reference.

FIELD OF THE INVENTION

The present invention relates generally to the field of storage of isolated blood components and more specifically to improved methods for storage of platelets.

BACKGROUND OF THE INVENTION

Platelets are anucleate bone marrow-derived blood cells that protect injured mammals from blood loss by adhering to sites of vascular injury and by promoting the formation of plasma fibrin clots. Humans depleted of circulating platelets by bone marrow failure suffer from life threatening spontaneous bleeding. Less severe deficiencies of platelets, such as thrombopenia, contribute to bleeding complications following trauma and surgery.

A major advance in medical care over a half-century ago was the development of techniques for platelet isolation and transfusion. However, unlike other transplantable tissues, refrigeration is deleterious to platelets. Accordingly, the current standard method for platelet storage to hold the platelets in a bag at room temperature with constant shaking, but this method is limited to five days of storage time. Thus, there is an ongoing unmet need for methods of increasing platelet storage time. The present invention meets this need.

SUMMARY OF THE INVENTION

The present invention provides improved methods for storing platelets and using stored platelets. Also provided are compositions comprising stored platelets. In one embodiment, the stored platelets are provided as platelet rich plasma. In connection with improved methods for storing platelets, the method generally comprises the steps of: i) obtaining a platelet concentrate from blood obtained from an individual; ii) holding the platelet concentrate under an atmosphere having a pressure of from 3.5 to 5 bars and comprising more than 65% xenon; and iii) holding the platelet concentrate of ii) at refrigeration temperatures.

The platelet concentrate can be held under gas-tight conditions at ambient temperature for a period of time, such as from ten seconds up to one hour, or more, and then refrigerated, such as at a temperature of from 3° C. to 6° C., including all integers there between, and all numbers between consecutive integers to the tenth decimal point (i.e., 3.1, 3.2, 3.3, etc.).

In one embodiment, the platelet concentrate is held under the atmosphere comprising at least 65% xenon at a partial or total pressure of 3.5 to 5 bars in a container for a period of at least one week at refrigerated temperatures.

The pressure of from 3.5 bars to 5 bars includes all integers there and all numbers between consecutive integers to the tenth decimal point (i.e., 3.6, 3.7, 3.8 bars, etc.).

The atmosphere comprising at least 65% xenon in various embodiments may comprise from 65% to 100% xenon, including all integers there between. In one embodiment, xenon is introduced into the atmosphere in a container containing the platelet concentrate, with or without concomitant removal of the existing gas/air, until the concentration of xenon in the atmosphere within the container is at least 65%, and wherein the atmosphere has at a total pressure of from 3.5 to 5 bars.

In order to prepare a platelet concentrate for use in transfusion, the method includes the additional step of allowing the atmosphere in which the platelet concentrate is held to equilibrate with ambient temperature and atmosphere. The method may further comprise reducing or eliminating residual xenon in the platelet concentrate. In one embodiment, reducing or eliminating residual xenon in the platelet concentrate is performed by applying vacuum to the platelet concentrate to reduce or eliminate residual xenon in the platelets. The vacuum is applied with sufficient pressure differential and for a period of time suitable to reduce or eliminate xenon that is not removed by only allowing the atmosphere of the container to equilibrate with ambient temperature and atmosphere. A vacuum of from 228 mmHg to 456 mmHg (i.e., 30% to 60% of one atmosphere of 760 mmHg at standard pressure and temperature) for a period of from thirty seconds to three hours may be used.

For practicing the invention, blood from an individual can be obtained using any suitable technique. Platelet concentrates can likewise be prepared from the blood of any individual using any of a variety of well known methods. For example, a blood sample from an individual can be centrifuged to obtain plasma rich platelets to be used as the platelet concentrate.

The platelet concentrate can be present in the atmosphere comprising the xenon in any suitable container. Suitable containers may be rigid or flexible containers. A non-limiting example of a flexible container is a bag. In particular embodiments, the container is gas-impermeable and sealable, and is thus capable of maintaining gas-tight conditions within the container. An alternative embodiment provides for use of a sealable, gas-permeable container, such as a bag, that is itself held in a gas impermeable container that is capable of maintaining gas-tight conditions. It is preferable that the container has efficient thermal exchange properties such that the temperature of the platelets is rapidly equilibrated to any of the various temperatures in which the container may be held.

The atmosphere in which the platelets are held can be adjusted to comprise various amounts of xenon using any suitable device/system. The device/system may additionally include one or more components used for altering, reducing or eliminating the atmosphere comprising xenon from the container and/or for exposing the platelet concentrate to a vacuum.

The platelet concentrate can be cooled using any suitable method, device or system. The platelet concentrate can be cooled to any temperature from 3° C. to 6° C., including all integers there between, and all numbers between consecutive integers to the tenth decimal point (i.e., 3.1, 3.2, 3.3 degrees, etc.). In one embodiment, the container is cooled to 4° C.

It will be recognized that the platelets and those substances that come into contact with the platelets should be kept sterile.

In one embodiment, the platelet concentrate is held in a container in the atmosphere comprising xenon at a refrigerated temperature from 3° C. to 6° C. under gas-tight conditions for a period of one week or longer, such as for two weeks. The platelet concentrate remains suitable for transfusion to an individual in need of platelet transfusion over this period. It will also be recognized that the platelet concentrate has other potential uses, such as for screening test agents as candidates for use as platelet aggregation and/or platelet activation inhibitors or promoters. Thus, platelet concentrates prepared according to the method of the invention could be utilized in, for example, high-throughput assays to screen a plurality of test agents for desirable characteristics in respect of modifying platelet function.

Before use, the atmosphere in which the platelet concentrate is held is allowed to equilibrate with ambient temperature and atmosphere. Ambient pressure at sea level is 1013.2 millibars, but can vary according to location. "Ambient pressure" therefore refers to the pressure of the atmosphere surrounding the platelet concentrate once the experimentally increased pressure in the atmosphere under which the platelets are held is released. It is therefore considered that the ambient pressure with which the platelets are equilibrated is equivalent to the ambient pressure at the physical location (i.e., ambient pressure in a laboratory) where the stored platelet concentrate is being prepared. It will be recognized that the platelets can be prepared in a temperature and humidity controlled room.

"Ambient temperature" means the temperature of the physical location (i.e., laboratory room temperature) where the stored platelet concentrate is being prepared. Ambient temperature can vary. In certain embodiments, ambient temperature can be from 18° C. to 26° C., including all integers there between, and all numbers between consecutive integers to the tenth decimal point. In a particular embodiment, ambient temperature is 23° C.

"Ambient atmosphere" means the composition of the atmosphere at a physical location (i.e., the composition of laboratory room air).

In another embodiment, the invention provides a platelet concentrate prepared according to the method of the invention. In general, the platelet concentrate is refrigerated, comprises xenon, and has been isolated from an individual for at least seven days. The platelet concentrate can be provided in a container containing an atmosphere that is comprised of more than 65% xenon. In one embodiment, the xenon in the atmosphere in the container has a partial or total pressure of from 3 to 5 bars, and is stored for up to two weeks, or more, at a refrigerated temperature of from 3° C. to 6° C. The platelet concentrate is accordingly expected to be useful in platelet transfusion therapies after storage for at least 14 days. Prior to transfusion, the platelet concentrate may be mixed with any suitable agent that is used in platelet transfusion therapy.

The individual receiving the transfusion may be any mammal in need of platelets and may suffer from any condition that results in platelet deficiency. In one embodiment, the mammal receiving the transfusion is a human.

BRIEF DESCRIPTION OF THE FIGURE

FIG. 1 provides a graphical representation of the time dependence of pressure changes under the two different pressure conditions. "Optimal" represents xenon at 4 bars at 4° C. "St. Clathrates" represents xenon at 5.4 bars at 4° C. Seven days of measurements are depicted on the graph. The slope of the "2-week" line remained the same over the second week.

DETAILED DESCRIPTION OF THE INVENTION

The present invention provides improved methods for storing platelets, as well as compositions comprising stored platelets. The method is based on our discovery that treatment of platelets in an atmosphere comprising xenon under certain pressures and temperatures as further described herein imparts to the platelets the ability to withstand refrigeration temperatures for at least two weeks, yet still retain properties that are indicative of suitability of the stored platelets for use in transfusions. For example, platelet concentrates treated using the method of the invention exhibit superior induced aggregation as compared to control platelets that are not treated with xenon. Further, our data demonstrate that platelet concentrates treated using the method of the invention have undergone minimal or no activation during storage as evidenced by reduced expression of surface markers that are indicative of platelet activation. In particular, activation of platelets is associated with platelet surface expression of CD62 (P-selectin) and CD41. CD62 is a molecule that is quickly mobilized to platelet cell surfaces in response to a variety of inflammatory or thrombogenic agents. CD41 is the α subunit of the CD41/CD61 complex (GPllb-llla), which is a calcium-dependent, non-covalently associated heterodimer. The activated CD41/CD61 complex is a receptor for von Willebrand factor, soluble fibrinogen and fibronectin, and is known to play a central role in platelet aggregation and activation. Therefore, activated platelets have surface detectable CD62 and CD41 which can be used as targets in immunoassays to determine whether platelets have undergone activation during storage, which significantly compromises their usefulness in transfusions.

We analyzed platelet activation using a standard methodology comprising immunostaining platelets for CD62 and CD41 and subsequent analysis by flow cytometry. (An example of the general method is provided in Shattil et al. (1987) Blood Vol. 70 p 307-315, from which the description of antibody staining and flow cytometry analysis is incorporated herein by reference.) Our data demonstrate two-fold less surface CD62 and CD41 over control platelet concentrates that are not treated with xenon. Thus, it will be recognized by those skilled in the art that the invention provides stored platelet preparations that are useful for treating individuals in need of platelet transfusion therapy. It is therefore considered that practicing the method of the invention transforms a platelet concentrate that would not ordinarily tolerate refrigeration into a platelet concentrate that can withstand refrigeration such that the platelet concentrate remains useful for transfusions after being stored at refrigerated temperature for at least two weeks. It will also be recognized that the platelet concentrate has other potential uses, such as in high-throughput assays to screen a test agents for the capability to modify platelet function.

Additionally, in contrast to previous approaches, the present invention does not require addition of starches, such as UDP-galactose, or anti-aggregation agents to the platelet concentrate. Moreover, our data demonstrate that replacing with xenon most or all of the oxygen in the environment in which the platelets are stored is more advantageous than replacing most or all of the oxygen with argon, which, like xenon, is also a noble gas. This result indicates that the benefits of the present invention are not merely due to reducing or eliminating oxygen from the environment in which the platelets are stored, and highlights an unexpected advantage of using xenon in our method of platelet preservation. In this regard, and without intending to be bound by any particular theory, it is considered that holding the platelet concentrate in a container containing an atmosphere adjusted to comprises at least 65% xenon at a partial or total pressure of 3.5 to 5 bars results in formation of metastable xenon clathrate structures, but similar xenon containing atmospheres at higher pressures result in formation of stable xenon clathrates, which are deleterious to stored platelets. Further, since the platelets can be stored as a platelet rich plasma, they are suitable for use in transfusions without having to be re-suspended or mixed with artificial media to compensate for preservative agents used during storage.

In general, the method comprises: i) obtaining a platelet concentrate from blood obtained from an individual; ii) holding the platelet concentrate under an atmosphere having a pressure of from 3.5 to 5 bars and comprising more than 65% xenon; and iii) holding the platelet concentrate of ii) at refrigeration temperatures.

In one embodiment, the atmosphere under which the platelet concentrate is held ia adjusted so as to have a pressure of from 3.5-5 bars and to comprise more than 65% xenon, wherein the xenon can have a partial or total pressure of 3.5 to 5 bars. The platelet concentrate may be first held for a period of at least 10 seconds and preferably for up to one hour at ambient temperature, after which the platelet concentrate is held at refrigeration temperatures under gas tight conditions for a period of at least one week. The refrigeration temperatures can be from 3° C. to 6° C., including all integers there between, and all numbers between consecutive integers to the tenth decimal point for a period of at least one week.

In various embodiments, the atmosphere which comprises at least 65% xenon, wherein the atmosphere has a pressure of from 3.5-5 bars comprises more than 65% xenon. In particular, the atmosphere can comprise up to 100% xenon, including all integers between 65 and 100%. In various embodiments, the xenon comprises at least 80, 81, 82, 83, 84, 85, 86, 87, 88, 89, 90, 91, 92, 93, 94, 95, 96, 97, 98, 99, or 100% of the atmosphere in a container in which the platelets are held. It will be recognized that, if the xenon comprises 100% of the gas in the atmosphere in the container, then xenon will alone account for the total pressure of the atmosphere in the container.

For practicing the invention, blood from an individual, such as any mammal including but not limited to a human, can be obtained using any suitable technique. Likewise, platelet concentrates can be prepared from the blood of the individual using any of a variety of well known methods. In one embodiment, platelet concentrate is platelet rich plasma (PRP). Some suitable techniques for isolating platelets and preparing platelet concentrates, such as PRP, are described in "Platelets: A Practical Approach" by S. P. Watson, Oxford University Press (1996), from which the description of techniques for isolating platelets and preparing platelet concentrates is hereby incorporated by reference.

The platelets may be held in any suitable container under an atmosphere which comprises at least 65% xenon at a pressure of from 3.5-5 bars.

Those skilled in the art will recognize that any container used for practicing the invention should be sterile. All other substances that come into contact with the platelets should also be kept sterile. In one embodiment, the container containing the platelet concentrate is a sterile container prior to adding the platelet concentrate. The atmosphere in the container can be adjusted by introducing gas that is passed through filters suitable to keep the gas free of contaminants that would render the gas non-sterile.

Suitable containers may be rigid, examples of which include but are not limited to test tubes, jars, flasks and chambers. The container is capable of maintaining a gas-tight environment. Thus, the container can be capable of being hermetically sealed. The container may also be a flexible, sealable container, an example of which includes but is not limited to a bag. In particular embodiments, the container is gas-impermeable and sealable, such as a sealable, gas impermeable bag. In an alternative embodiment, the container is a sealable gas permeable bag that is itself held in a gas impermeable container. It is preferable that the container used in the invention have efficient thermal exchange properties such that the temperature of the platelets is rapidly equilibrated to any of the various temperatures in which the container is placed and/or held.

In one embodiment, xenon is introduced into the atmosphere within a container, with or without concomitant removal of the existing gas/air, until the concentration of xenon in the gas atmosphere within the container is at least 65%. In one embodiment, the atmosphere in the container consists of xenon. In an alternative embodiment, the atmosphere may consist of xenon and trace impurities. Thus, in one embodiment, the atmosphere may consist essentially of xenon.

The gas-tight pressure of the atmosphere comprising at least 65% xenon under which the platelet concentrate is held during refrigeration is preferably from 3.5 bars to 5 bars, including all numbers between 3.5 and 5 to the tenth decimal point. In one embodiment, the xenon in the atmosphere provides a partial or total pressure of 4 bars.

When performing the method of the invention, any suitable system may be used for adjusting the atmosphere in which the platelets are held to provide an atmosphere comprising at least 65% xenon at a desired partial or total pressure of xenon. The general features of such systems include a reservoir for the gas, whereby the reservoir is preferable operably connected to a container containing the platelet concentrate and the atmosphere. Suitable gas systems may comprise components including but not limited to valves, pumps, fans, vents, and combinations thereof, as well as a controller for controlling the system components and thereby the amount of gas delivered to the container, and the rate at which the gas is delivered. The system may additionally include one or more components used for evacuation of the xenon comprising atmosphere from the container and/or for creating a vacuum in the container. The entire system or any component or portion of a component may be manually operated, or can be automated so as to be operated by computers and computer programs. Any portion of the device/system that comes into contact with the gas that is introduced into the container, as well as the gas itself, should be kept sterile.

The container in which the platelets can be held may be cooled using any suitable method, device or system at any refrigerated temperature, such as from 1° C. to 6° C. including all integers there between, and all numbers between consecutive integers to the tenth decimal point. It is preferable that the container is cooled to a temperature of from 3° C. to 6° C., whereby the temperature of the container (and thus presumptively the temperature of the platelets inside the container) will be from 3° C. to 6° C., including all integers there between, and all numbers between consecutive integers to the tenth decimal point. In one embodiment, the container is cooled to and held at 4° C.

The container may be held at any temperature from 3° C. to 6° C. under gas-tight conditions for a period of one week or longer, such as for two weeks. Thus, the invention is useful for storing platelets for 7, 8, 9, 10, 11, 12, 13, 14, or more days. Accordingly, it is expected that the method of the invention can facilitate storage of a platelet concentrate for longer than two weeks, whereby the platelet concentrate remains suitable for transfusion to an individual in need of platelet transfusion therapy.

After the atmosphere in which the platelet concentrate is held is allowed to equilibrate with ambient temperature and atmosphere, residual xenon that may be in the platelets may be reduced or eliminated using any suitable technique. Examples of suitable techniques include but are not limited to bubbling a xenon-free gas through the platelet concentrate, or a by application of vacuum pressure inside a container containing the platelet concentrate using any suitable vacuum device/system. The platelets could be placed into a different container for vacuum treatment. In general, for exposure to vacuum, the container may be adapted to be connected to a vacuum pump which may or may not be a component of the system that is used to introduce the xenon gas into the container. The vacuum pump is capable of creating a vacuum sufficient to reduce or eliminate residual xenon (i.e., xenon that is not released by only allowing the atmosphere in the container to equilibrate with ambient temperature and atmosphere) from the platelet concentrate. A vacuum of from 228 mmHg to 456 mmHg (i.e., 30% to 60% of one atmosphere of 760 mmHg at standard pressure and temperature) for a period of from thirty seconds to three hours may be used.

The invention also provides a refrigerated composition comprising a platelet concentrate prepared according to the method of the invention. Generally, the composition comprising the platelet concentrate is refrigerated, comprises xenon, and has been isolated from an individual for at least seven days. The platelet concentrate may be provided in a container containing an atmosphere that has been adjusted to comprise more than 65% xenon. The xenon in the atmosphere in the container may have a partial or total pressure of from 3 to 5 bars. Thus, it will recognized that although the platelet concentrate may have been refrigerated according to the method of the invention under a pressure of 3.5 bars, the pressure may reduce over time, owing to dissolution of xenon in the atmosphere in the container into platelet membranes. The composition comprising the platelet concentrate can be stored at refrigerated temperatures for up to two weeks, or more. In one embodiment, the refrigerated temperature is from 3° C. to 6° C., including all integers there between, and all numbers between consecutive integers to the tenth decimal point The platelet concentrate is expected to be useful in platelet transfusion therapies after storage for at least 14 days.

A container containing the platelet concentrate may be transported to a location and/or individual or entity and from there distributed to health care personnel for use in platelet transfusion therapies, or the platelet concentrate may be transported directly to a health care provider. In any case, for use in transfusion therapies, the atmosphere in the container is allowed to equilibrate with ambient temperature and atmosphere, after which residual xenon may be reduced or eliminated from the platelets to prepare the platelets for transfusion into an individual as set forth above. It is contemplated that the platelet concentrate stored according to the method of the invention and subsequently allowed to equilibrate with ambient temperature and atmosphere could be further held at ambient pressure and temperature if desired or necessary for a period of time prior to transfusion, such as for up to five days. Prior to transfusion, the platelet concentrate could be mixed with any suitable agent that is used in transfusion therapy. If the platelet concentrate comprises a PRP, the PRP may be used directly for transfusion, or may be mixed with any suitable buffer, or any other agent that is useful for platelet transfusions.

The individual receiving the transfusion may be any mammal in need of platelets. In various embodiments, the mammal may be afflicted with bone marrow failure caused by disease or chemotherapy, or may be suffering from any other platelet deficiency, one non-limiting example of which is thrombopenia. In one embodiment, the mammal receiving the transfusion is a human.

The following Example is meant to illustrate, but not limit the invention.

EXAMPLE 1

This Example demonstrates one embodiment of the invention. Blood was obtained by puncturing a rabbit marginal ear vein and collecting blood in a sterile vacuum tube. About 10-15 ml of blood was used, although the amount taken from any particular individual can be varied by the skilled artisan according to routine considerations, such as the size of the individual and the intended use of the platelets prepared according to the method of the invention.

The blood was centrifuged at a speed of approximately 200 g for 10 minutes to separate red blood cells (RBC) and platelet rich plasma (PRP). The PRP was transferred to another tube.

Two microliters of PRP can were used to count cells essentially as described in Born et al. (J. Physiol. (1963) Vol. 168, pp 178-195). An additional two microliters were used for antibody staining and flow cytometry analysis performed essentially as reported in Shattil et al. (1987) *Detection* Blood Vol. 70 p 307-315.

For determining platelet aggregation, approximately 250 microliters of PRP were used for a pre-treatment aggregation test. The remaining PRP was transferred to test tubes in which the atmosphere was adjusted to include xenon under two distinct pressures (4 bars of total pressure created by introducing 99.999% xenon into the test tube in a first set of experiments, and 5.3 bars of total pressure, also created by introducing 99.999% xenon into the test tube, in a second set of experiments). For adjusting the atmosphere in the containers, the test tubes were covered with rubberized caps that were punctured for introducing xenon. The test tubes were put into an experimental chamber and the atmosphere in the test tubes was adjusted by filling the test tubes with xenon using a 0.2-micrometer aseptic filter. Pressure changes in the tubes were measured using a manometer. Negative controls (no adjustment of the composition of the atmosphere in which the platelets were held) were also performed.

The chambers were shaken at 150-200 rpm on a Biosan OS-10 orbital shaker for one hour at ambient temperature (approximately 23° C.) to dissolve xenon in the PRP. The experimental chambers were then stored at approximately 4° C. with shaking at 50-70 rpm using a Biosan OS-10 orbital shaker and removed at one and two week time points for experiments under 4 bars of xenon pressure. The experiment using the initial xenon pressure of 5.3 bars were stored at 4° C. for 1 week.

After storage, the chambers were removed from refrigeration and kept at ambient temperature (approximately 23° C.) for 30 minutes with shaking at approximately 150-200 rpm. The atmosphere was then slowly allowed to equilibrate with ambient pressure of a period of 30 minutes by allowing the atmosphere in the chamber and in the test tubes to equilibrate with the atmosphere outside the test tubes through a specially adapted valve. Once the atmosphere in the chambers and test tubes equilibrated with ambient pressure, vacuum was applied for approximately three minutes at approximately 380 mmHg to remove residual xenon from the PRP.

Analysis of platelet function after storage included platelet counting at a hemocytometer, platelet aggregation tests using ADP and epinephrine as aggregation inducing agents, with manual counting and analysis using an aggregometer, and CD62p/CD61 antibody staining, with subsequent flow cytometry analysis on Epic XL, Beckman-Coulter generally as described in Shattil et al. (1987) Blood Vol. 70 p 307-315. Two ml of platelets were stained using anti-CD62p and anti-CD61 antibodies obtained from commercial vendors. The results were as follows.

FIG. 1 provides a graphical representation of the time dependence of pressure changes in the atmospheres in which the platelets were held under the two different pressure conditions. As can be seen from FIG. 1, there was negligible pressure change in experiments in which the containers contained an atmosphere at 4 bars of total pressure created by introduction of xenon into the atmosphere in the containers. Without intending to be bound by any particular theory, it is considered that, if the xenon dissolved in the PRP could form clathrate structures, only metastable clathrates structures were formed under 4 bars of xenon. In contrast, and again without intending to be bound by any particular theory, the time dependence of pressure changes in the containers containing an atmosphere with a total pressure of 5.3 bars created by introducing xenon into the containers showed a pronounced drop in pressure, which suggests that a substantial amount of xenon formed stable clathrates in the PRP, particularly since at the conclusion of storage when the temperature was allowed to equilibrate with ambient temperature, xenon that was presumably bound in clathrates at the low temperature appears to have been released, as indicated by the pressure rise on the graph.

Subsequent to allowing the atmosphere in the experimental and control tubes to equilibrate with ambient pressure and temperature, the PRP samples were analyzed using conventional hemocytometer based cell counting, induced aggregation analysis using ADP and epinephrine, whereby aggregation was determined using manual counting and aggregometer analysis according to standard techniques, and by cd62p/cd61 immunostaining and flow cytometry analysis performed on an Epic XL, Beckman-Coulter cytometry machine. The cdc62p/cd61 analysis was performed using commercially available antibodies and generally according to the known method reported in Shattil et al. (1987) *Detection of activated platelets in whole blood using activation-dependent monoclonal antibodies and flow cytometry*. Blood Vol. 70 p 307-315. Results of these experiments are presented in Table 1.

TABLE 1

| Parameter | Input | 7 days NG control | 7 days Xe, 4 bars, 4° C. | 7 days Xe, 5.3 bars, 4° C. | 14 days NG control | 14 days Xe, 4 bars, 4° C. |
|---|---|---|---|---|---|---|
| Cell number | 100% | 59.3% | 77.5% | 12.6% | 54 | 59% |
| Aggregation (ADP/epinephrine) | 100% | 83% | 83% | — | 35% | 54.5% |
| Cd41/62p | 13% | 57% | 39% | — | 63% | 33% |

In Table 1, "Input" represents pre-treatment/storage measurements. Cell number and Aggregation induced by ADP/epinephrine before performing the method are used to set 100% values. For the Cd41/62p immunostaining/cell sorting, 13% of the cells exhibit these markers of platelet activation prior to performing the method. NG=no gas. The NG controls were performed without using xenon, and without application of pressure, but at the refrigerated temperature (4° C.).

The results presented in Table 1 demonstrate that, in the case of PRP storage in an atmosphere at 4 bars of xenon pressure at 4° C., the number of intact cells is higher compared to control samples both after 1 week storage and 2 weeks, and is markedly higher than for cells subjected to 5.3 bars of xenon pressure. Without intending to be bound by any particular theory, it is considered that decomposition of stable clathrates and gas release after 5.3 bar xenon treatment is lethal to platelets and is responsible for the low cell count.

The level of induced aggregation is similar after 1 week storage for the 4 bar xenon atmosphere sample and the control sample. However, after 2 weeks of storage, induced aggregation is about 20% higher for the 4 bar xenon treated sample, demonstrating an advantage of subjecting the cells to 4 bar xenon treatment, relative to using no gas. Measurements of aggregation were not performed for the 5.3 bar xenon atmosphere treated cells, due to the low cell count after 1 week of treatment. As to the level of spontaneous aggregation measured by Cd41/62p immunostaining and flow cytometry, the results demonstrate two-fold better inhibition of spontaneous activation in the xenon 4 bar atmosphere treated samples relative to the NG control, which is indicative of the suitability of the platelets for use in transfusions.

As shown in Table 2, we also determined that ADP/Epinephrine induced aggregation improves by 20% if residual xenon is evacuated from the PRP by application of vacuum. This indicates that xenon has properties that inhibit aggregation activity of stored platelets, which is believed to spare stored platelets from spontaneous aggregation during storage.

TABLE 2

|  | Input | One week NG control | 7 days Xe, 4 bars, 4° C. | 7 days Xe, 4 bars, 4° C. with three minutes vacuum application |
|---|---|---|---|---|
| Aggregation (ADP/epinephrine), % | 83 | 66 | 53 | 72 |

In view of the result obtained in Table 2, we performed another set of experiments to compare the properties of xenon to argon in ADP-induced platelet aggregation assays, the results of which are depicted in Table 3.

TABLE 3

| Sample/parameter | # cells (*106 cells/ul) | Aggregation % |
|---|---|---|
| Control No Gas (for Xe) | 628 | 100% |
| Xenon | 674 | 87% |
| Control No Gas (for Ar) | 596 | 90% |
| Argon | 594 | 100% |

The experiments summarized in Table 3 were performed using an atmosphere of 4 bars total pressure created by introducing xenon or argon into the containers using essentially the same techniques as for the experiments described for Tables 1 and 2, except the PRP samples were cooled to 4° C. and held at approximately in an atmosphere of 3.8 bar xenon for 7 days. In this experiment, the initial partial pressure of xenon was 4 bars, but the pressure dropped to 3.8 bars during storage, presumably due to dissolution of xenon into the platelets from the atmosphere in the container. In order to determine whether xenon is superior to argon in inhibiting spontaneous platelet activation during storage, we slowly warmed the PRP samples to ambient temperature and pressure and then analyzed their response in ADP induced-aggregation experiments. As can be seen from Table 3, when residual xenon is presumably present in the PRP due to omitting the vacuum step, the platelets are less sensitive to ADP-induced aggregation as compared to platelets that have been subjected to argon. This it taken to mean that the residual xenon is superior to argon in protecting against spontaneous platelet activation, which is known to be associated with platelet aggregation. Thus, the results presented in Table 3 show that the method of the invention likely protects at least some platelets from spontaneous activation during storage, and also demonstrates that the benefits of the present invention are not solely because of a reduction of some or all of the oxygen in the environment in which the platelets are stored.

The invention has been illustrated by the foregoing examples. Those skilled in the art will be able to make minor modifications as necessary to practice the invention without departing from the spirit of the invention.

We claim:

1. A method for preserving platelets comprising:
   i) obtaining a platelet concentrate from blood obtained from an individual;
   ii) holding the platelet concentrate under an atmosphere having a pressure of from 3.5 bars to 5 bars and comprising more than 65% xenon; and
   iii) holding the platelet concentrate of ii) at refrigeration temperatures.

2. The method of claim 1, comprising holding the platelet concentrate under the atmosphere comprising more than 65% xenon at the refrigerated temperatures for a period of at least one week under gas-tight conditions.

3. The method of claim 1, wherein the atmosphere comprises from 90% to 100% xenon.

4. The method of claim 3, wherein the xenon has a partial pressure or total pressure of 3.5 to 5 bars.

5. The method of claim 1 further comprising, prior to performing iii), holding the platelet concentrate at ambient temperature under a pressure of from 3.5 to 5 bars in an atmosphere comprising more than 65% xenon for from 10 seconds to one hour.

6. The method of claim 1, wherein the platelet concentrate and the atmosphere having a pressure of from 3.5 to 5 bars and comprising more than 65% xenon and are held in a container at the refrigerated temperatures for at least one week.

7. The method of claim 6, wherein the refrigerated temperature is from 3° C. to 6° C.

8. The method of claim 6, wherein subsequent to holding the container at the refrigerated temperature for a period of at least one week, allowing the atmosphere to equilibrate with ambient temperature and atmosphere.

9. The method of claim 8, further comprising reducing or eliminating residual xenon in the platelet concentrate.

10. The method of claim 9, wherein the reducing or eliminating residual xenon in the platelet concentrate comprises applying vacuum to the platelet concentrate.

11. The method of claim 6, wherein the container is selected from the group of containers consisting of a test tube, a jar, a chamber, and a bag.

12. A refrigerated composition comprising a platelet concentrate, wherein the platelet concentrate is in a container containing an atmosphere, wherein xenon comprises more that 65% of the atmosphere and wherein the platelet concentrate has been isolated from an individual for at least seven days.

13. The composition of claim 12, wherein the xenon in the atmosphere in the container has a partial or total pressure of from 3 to 5 bars.

14. The composition of claim 13, wherein the composition is refrigerated at a temperature of from 3° C. to 6° C.

* * * * *